United States Patent
Lesins et al.

[11] Patent Number: 6,130,361
[45] Date of Patent: Oct. 10, 2000

[54] REDUCING META CONTENT OF ISOMERIC MIXTURES OF HALO SUBSTITUTED TOLUENES

[75] Inventors: Viesturs Lesins, Buffalo; David Y. Tang, East Amherst; Arthur H. Morth, Grand Island; Mark E. Lindrose, Buffalo; William L. Rueter, Niagara Falls; Frank Bermel, Orchard Park, all of N.Y.

[73] Assignee: Occidental Chemical Corporation, Dallas, Tex.

[21] Appl. No.: 09/193,755

[22] Filed: Nov. 17, 1998

[51] Int. Cl.[7] .............................. C07C 17/38; C07C 20/00
[52] U.S. Cl. .......................... 570/211; 570/206; 570/210
[58] Field of Search ................................. 570/206, 210, 570/211

[56] References Cited

U.S. PATENT DOCUMENTS 3,655,783  4/1972  Bacha .
4,827,058  5/1989  Mais et al. .............................. 570/211

*Primary Examiner*—Alan Siegel
*Attorney, Agent, or Firm*—Anne E. Brookes; Richard D. Fuerle

[57] ABSTRACT

Disclosed is a method of separating the meta isomer of a halotoluene having the general formula

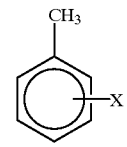

from a mixture with at least one other isomer, where X is Cl or Br. About 0.0001 to about 5 wt % of a Friedel-Crafts catalyst is added to the mixture and the mixture is exposed to a brominating agent which preferentially brominates the meta isomer. The mixture is then heated at a temperature above the boiling point of the other isomers but below the boiling point of the brominated meta isomer.

20 Claims, No Drawings

REDUCING META CONTENT OF ISOMERIC MIXTURES OF HALO SUBSTITUTED TOLUENES

BACKGROUND OF THE INVENTION

This invention relates to a method of reducing the content of the meta isomer of a halo substituted toluene in a mixture with other isomers. In particular, it relates to exposing the mixture to a brominating agent under conditions such that the meta isomer is preferentially brominated.

Commercial parachlorotoluene (PCT) is made by chlorinating toluene. After distilling off the unreacted toluene and most of the orthochlorotoluene (OCT), the product is primarily PCT, but small amounts of metachlorotoluene (MCT) and OCT are also present, typically about 0.5 to about 1 wt % MCT and about 0.5 to about 1 wt % of the OCT. PCT is used as an intermediate in the preparation of pharmaceuticals, paint pigments, herbicides, and other chemicals. While the presence of small amounts of the OCT is usually innocuous, it has been found that the presence of MCT can deleteriously affect the properties of the chemicals made from PCT. Unfortunately, the boiling point of MCT is close to the boiling point of PCT and the two isomers cannot be easily separated.

In U.S. Pat. No. 4,827,058, herein incorporated by reference, a chlorotoluene isomeric mixture is chlorinated in the presence of a Friedel-Crafts catalyst at a temperature of 0° C. up to the boiling point of the mixture. The MCT chlorinates to dichlorotoluene to a much greater extent than does the OCT or the PCT. The PCT-OCT mixture is then separated from the higher boiling dichlorotoluenes (DCT) by distillation.

SUMMARY OF THE INVENTION

We have discovered that meta halo substituted toluenes and can be separated from an isomeric mixture by exposing the mixture to a brominating agent under conditions such that the meta isomer is preferentially brominated. While bromine is less effective than chlorine in aromatic substitution, we have found that it is more selective for the meta isomer in this reaction than is chlorine. Thus, we are able to remove more of the meta isomer while halogenating less of the desirable para isomer than was possible using chlorine.

We have also found that the bromination reaction is unusually fast, which is a processing advantage. In addition, we have found that when the brominating agent is bromine, the byproduct, hydrogen bromide, is not evolved and can be converted in situ to additional brominating agent by adding chlorine. In this way, expensive bromine is not wasted.

DESCRIPTION OF THE PREFERRED EMBODIMENTS

The starting substrate for the process of this invention is a mixture of isomers having the general formula

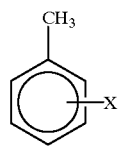

where X is Cl or Br, but is preferably chlorine as those compounds are commercially more important. While the process of this invention will work with mixtures of isomers that contain almost any amount of the meta isomer, it is most practical for mixtures of isomers that contain about 0.01 to about 10 wt % of the meta isomer.

About 0.0001 to about 5 wt % of a Friedel-Crafts catalyst is added to the isomeric mixture. Preferably, about 0.001 to about 1 wt % catalyst is used as less is less effective and more is usually unnecessary. Examples of suitable Friedel-Crafts catalysts include the chlorides of manganese, molybdenum, titanium, iron, aluminum, zinc, tin, antimony, and mixtures thereof. The preferred catalyst is ferric chloride as it is inexpensive, works well, and is often the catalyst used to chlorinate toluene.

It is preferable to also use about 0.001 to about 5 wt % of an optional cocatalyst. Preferably, about 0.01 to about 1 wt % of the cocatalyst is used. Examples of cocatalysts include sulfur and sulfur compounds such as diphenylsulfide, disulfur dichloride, thianthrene, thianthrene derivatives, phenoxathiin, phenoxathiin derivatives, phenothiazine, phenothiazine derivatives, iodine, and iodine compounds. The preferred cocatalyst is thianthrene as it is often used in the chlorination of toluene.

Examples of suitable brominating agents include liquid or gaseous bromine, BrCl, and sulfuryl bromide ($S_2Br_2$), The preferred brominating agents are liquid bromine and BrCl as they are inexpensive and effective. About ½ to about 10 equivalents of brominating agent can be used per equivalent of the meta isomer that is present in the mixture. It is preferable to use about 2 to about 5 equivalents of the brominating agent per equivalent of meta isomer that is present in the mixture as less may leave some meta isomer unbrominated and more may brominate some of the para isomer. Generally, proportionally less brominating agent is required at higher meta concentrations.

If the starting material was prepared by halogenating toluene, unreacted toluene is preferably removed first to prevent its bromination. The brominating agent is added to the mixture of isomers, catalyst, and optional cocatalyst, which can be, for example, at a temperature of about 0° C. to reflux. The preferred temperature range is between room temperature and about 50° C. as at lower temperatures the reaction is slow, although the selectivity is better, while the reverse is true at higher temperatures. The brominated agent can be added before or after the mixture is heated.

The bromination produces a bromochloro or dibromo substituted toluene and usually a halogenated byproduct, e.g., hydrogen bromide if $Br_2$ is used or HCl if BrCl is used. We have found that when bromine is used, a substantial portion of the HBr that is formed does not evolve but remains in solution. The addition of chlorine gas to the solution results in the formation of additional bromine or BrCl in situ. Thus, to prevent the evolution and loss of expensive bromine, one can use about ½ equivalent of bromine, wait until it reacts, then add about ½0 equivalent of chlorine. The bromination reaction is unexpectedly rapid (about 15 minutes) and can be followed by gas chromatography (GC) to determine its completion. The lower boiling unreacted para and ortho isomers are then distilled off, leaving behind the higher boiling brominated meta isomer. Using the method of this invention, the meta content can be reduced to less than 0.1 wt %.

The following examples further illustrate this invention.

EXAMPLES 1 to 6

A reactor fitted with an agitator and a gas outlet was charged with a chlorotoluene mixture as summarized in the table below. The catalyst and 0.210 mL of $S_2Cl_2$ were added to the chlorotoluene mixture and the solution was allowed to equilibrate to the designated temperature. Then the bromine was added and the reactor was sampled at the stated time and analyzed.

reaction was monitored by the evolution of heat. Based on the observed heat effects, the reaction time to reach 95% completion was 6.5 minutes. Reaction time to 99.9% completion was 15.5 minutes.

| Example | Chloro-toluene (g) | FeCl$_3$ (g) | Br$_2$ (mL) | Temp. (° C.) | Time (hrs) | GC Analysis (Area %) | | | |
|---|---|---|---|---|---|---|---|---|---|
| | | | | | | OCT | MCT | PCT | Others |
| Initial | | | | | | 1.036 | 0.516 | 98.324 | 0.124 |
| 1 | 153.5 | 0.1438 | 2.0 | 46 | 0.5 | 0.988 | 0.007 | 96.129 | 2.926 |
| 2 | 153.8 | 0.1453 | 1.0 | 46 | 1.0 | 0.989 | 0.082 | 97.529 | 1.400 |
| 3 | 153.8 | 0.1456 | 1.5 | 31 | 2.0 | 0.962 | 0.012 | 96.896 | 2.130 |
| 4 | 154.1 | 0.1484 | 2.0 | 11 | 3.0 | 0.988 | 0.055 | 97.399 | 1.558 |
| 5 | 153.9 | 0.1445 | 1.0 | 11 | 3.0 | 1.000 | 0.086 | 97.720 | 1.194 |
| 6 | 154.0 | 0.1411 | 0.8 | 0 | 6.0 | 1.526 | 0.091 | 98.080 | 0.303 |

EXAMPLE 7 and 8

A reactor fitted with an agitator and a gas outlet was charged with a chloroluene mixture as summarized in the table below. The catalyst was added to the chlorotoluene mixture and allowed to equilibrate to 30° C., followed by 1.5 mL of bromine. The reactor was sampled at the stated time and analyzed.

| Example | Chloro-toluene (g) | FeCl$_3$ (g) | Time (hrs) | GC Analysis (Area %) | | | |
|---|---|---|---|---|---|---|---|
| | | | | OCT | MCT | PCT | Others |
| Initial | | | | 1.036 | 0.516 | 98.324 | 0.124 |
| 7 | 154.1 | 0.0458 | 4.0 | 0.989 | 0.064 | 96.943 | 2.004 |
| 8 | 154.0 | 0.0983 | 3.0 | 0.968 | 0.013 | 96.786 | 2.233 |

EXAMPLE 9 and 10

A reactor or fitted with an agitator and a gas outlet was charged with a chloroluene mixture as summarized in the table below. The catalyst was added to the mixture and allowed to equilibrate to 30° C., followed by the bromine. The reactor was sampled at the stated time and analyzed.

| Example | Chloro-toluene (g) | FeCl$_3$ (g) | Br$_2$ (mL) | Time (hrs) | GC Analysis (Area %) | | | | |
|---|---|---|---|---|---|---|---|---|---|
| | | | | | Toluene | OCT | MCT | PCT | Others |
| Initial | | | | | 10.913 | 42.883 | 0.252 | 45.913 | 0.039 |
| 9 | 155.1 | 0.0975 | 9.0 | 2.0 | 0 | 41.079 | 0.027 | 45.511 | 13.382 |
| Initial | | | | | 0.028 | 48.061 | 0.282 | 51.588 | 0.041 |
| 10 | 154.7 | 0.0927 | 1.5 | 3.0 | 0 | 46.506 | 0.047 | 51.247 | 2.199 |

The above experiments show that the method of this invention is very effective in reducing the MCT content of an isomeric mixture of chlorotoluenes.

EXAMPLE 11

A reaction calorimeter was charged with 714 g of PCT and 0.66 g of FeCl$_3$. The temperature was adjusted to 30° C. and 22.0 parts of liquid Br$_2$ were added in single dose. The

EXAMPLE 12

To a reactor was charged 1069.8 g PCT and 0.5224 g FeCl$_3$. The temperature of the mixture was adjusted to 30° C. and 31.6 g of bromine were allowed to react to completion. The resulting mixture was removed from the reactor and 863.3 g were transferred to a still pot and distilled at 100 mm Hg through a distillation column with 10 sieve plates. The results of the distillation are shown in the table below.

| | Takeoff | | GC Area % | | | |
|---|---|---|---|---|---|---|
| | (grams) | Rate (%) | OCT | MCT | PCT | Others |
| First Fraction | 17.7 | 50 | 1.63 | 0 | 98.28 | 0.09 |
| Second Fraction | 398.5 | 50 | 1.15 | 0 | 98.85 | |
| Third Fraction | 158.8 | 50 | 0.87 | 0 | 99.13 | |
| Fourth Fraction | 152.3 | 40 | 0.63 | 0 | 99.37 | |
| Fifth Fraction | 45.1 | 33 | 0.25 | 0 | 99.75 | |
| Final Still Pot | 62.2 | | 0.09 | 0 | 96.61 | 3.3 |
| Initial Para-chlorotoluene | | | 0.96 | 0.39 | 98.64 | 0.01 |

EXAMPLE 13

To a reactor was charged PCT and enough FeCl$_3$ to make a 500 ppm solution. Chlorine or bromine was added to the reaction mixture at 23° C. and the mixture sampled. Results illustrating the increased effectiveness of bromine are illustrated below. At the point where chlorine and bromine reduced the PCT concentration to 97.5 wt %, 0.4 wt % MCT remained in the chlorine treated sample while the assay for the bromine treated MCT was below the detection limit.

|  | GC Area % | | | |
| --- | --- | --- | --- | --- |
|  | OCT | MCT | PCT | DCT |
| Starting Material | 1.4 | 0.5 | 98.1 | 0.0 |
| Chlorine | 1.4 | 0.4 | 97.5 | 0.7 |
| Bromine | 1.3 | 0.0 | 97.5 | 1.2 |

We claim:

1. A method of separating the meta isomer of a compound having the general formula

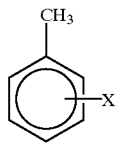

from a mixture with at least one other isomer, where X is Cl or Br, comprising (A) adding to said mixture about 0.0001 to about 5 wt % of a Friedel-Crafts catalyst;

(B) exposing said mixture to about ½ to about 10 equivalents of a brominating agent per equivalent of said meta isomer, whereby said meta isomer is preferentially brominated; and (C) heating said mixture to a temperature above the boiling point of said other isomers but below the boiling point of said brominated meta isomer.

2. A method according to claim 1 wherein X is Cl.

3. A method according to claim 1 wherein said brominating agent is liquid bromine.

4. A method according to claim 3 wherein about ½ equivalent of said bromine is used followed by about ½ equivalent of chlorine after said bromine has reacted.

5. A method according to claim 1 wherein said brominating agent is BrCl.

6. A method according to claim 1 wherein about 0.01 to about 10 wt % of said mixture is the meta isomer.

7. A method according to claim 1 wherein said catalyst is ferric chloride.

8. A method according to claim 1 wherein 0.001 to about 5 wt % of a cocatalyst is present.

9. A method according to claim 8 wherein said cocatalyst is thianthrene.

10. A method according to claim 1 wherein said bromination is performed at about 0° C. to reflux.

11. A method of reducing the content of metachlorotoluene in a mixture with parachlorotoluene comprising (A) adding to said mixture about 0.01 to about 1 wt % of a Friedel-Crafts catalyst;

(B) heating said mixture to a temperature between 0° C. and reflux;

(C) adding about 2 to about 5 equivalents of $Br_2$ or BrCl to said mixture per equivalent of said meta chlorotoluene; and (D) heating said mixture to a temperature above the boiling point of said parachlorotoluene but below the boiling point of said brominated metachlorotoluene.

12. A method according to claim 11 wherein said Friedel-Crafts catalyst is ferric chloride.

13. A method according to claim 11 wherein said mixture includes about 0.01 to about 1 wt % of a cocatalyst.

14. A method according to claim 13 wherein said cocatalyst is thianthrene.

15. A method according to claim 11 wherein liquid bromine is used in step (C).

16. A method according to claim 11 wherein BrCl is used in step (C).

17. A method of reducing the content of metachlorotoluene in a mixture with parachlorotoluene comprising (A) adding to said mixture about 0.01 to about 1 wt % of a Friedel-Crafts catalyst;

(B) heating said mixture to a temperature between 0° C. and reflux; and (C) adding about ¼ to about 5 equivalents of $Br_2$ to said mixture per equivalent of said meta chlorotoluene;

(D) after said $Br_2$ has reacted, adding about ½ equivalent of $Cl_2$ to said mixture react with said HB and form additional $Br_1$; and (E) heating said mixture to a temperature above the boiling point of said parachlorotoluene but below the boiling point of said brominated metachlorotoluene.

18. A method according to claim 17 wherein said Friedel-Crafts catalyst is ferric chloride.

19. A method according to claim 17 wherein said mixture includes about 0.01 to about 1 wt % of a cocatalyst.

20. A method according to claim 19 wherein said cocatalyst is thianthrene.

* * * * *

UNITED STATES PATENT AND TRADEMARK OFFICE
CERTIFICATE OF CORRECTION

PATENT NO. : 6,130,361
DATED : October 10, 2000
INVENTOR(S) : Viesturs Lesins et al.

It is certified that error appears in the above-identified patent and that said Letters Patent is hereby corrected as shown below:

Column 2,
Line 53, delete "equivalent" and substitute -- the amount --
Line 54, delete "½0 equivalent" and substitute -- the same equivalents --

Column 5, claim 4,
Line 36, delete "equivalent"
Lines 36 and 37, delete "½ equivalent" and substitute -- the same number of equivalents --

Column 6, claim 17,
Line 35, after "reacted" insert -- and formed HBr --
Lines 35 and 36, delete "about ½ equivalent of"
Line 36, delete "HB" and substitute -- HBr --
Line 37, delete "$Br_1$" and substitute -- $Br_2$ --

Signed and Sealed this

Ninth Day of October, 2001

*Attest:*

NICHOLAS P. GODICI
*Attesting Officer*    *Acting Director of the United States Patent and Trademark Office*